United States Patent [19]

Asakawa

[11] Patent Number: 4,507,403

[45] Date of Patent: Mar. 26, 1985

[54] PROCESS FOR PREPARATION OF METHANOL

[75] Inventor: Kazuo Asakawa, Niigata, Japan

[73] Assignee: Mitsubishi Gas Chemical Company, Inc., Tokyo, Japan

[21] Appl. No.: 529,653

[22] Filed: Sep. 6, 1983

Related U.S. Application Data

[63] Continuation of Ser. No. 344,932, Feb. 2, 1982, abandoned.

[30] Foreign Application Priority Data

Feb. 6, 1981 [JP]  Japan .................................. 56-16595

[51] Int. Cl.³ ........................ L07C 27/06; L07C 31/04
[52] U.S. Cl. ..................................... 518/713; 502/244; 502/87
[58] Field of Search ......................................... 518/713

[56] References Cited

U.S. PATENT DOCUMENTS

| | | |
|---|---|---|
| 1,681,750 | 8/1928 | Storch ................................. 518/713 |
| 3,326,956 | 6/1967 | Davies et al. ........................ 518/713 |
| 3,897,471 | 7/1975 | Herbert et al. ...................... 518/713 |
| 3,923,694 | 12/1975 | Cornthwaite ........................ 518/713 |
| 3,940,428 | 2/1976 | Connell et al. ...................... 518/713 |
| 4,107,089 | 8/1978 | Bondar et al. ....................... 518/713 |
| 4,111,847 | 9/1978 | Stiles .................................... 518/713 |
| 4,126,581 | 11/1978 | Sugier et al. ........................ 518/713 |

*Primary Examiner*—Howard T. Mars
*Attorney, Agent, or Firm*—Wenderoth, Lind & Ponack

[57] ABSTRACT

In a process for preparing methanol which comprises reacting a gaseous mixture containing hydrogen and either one or both of carbon monoxide and carbon dioxide in the gaseous phase in the presence of a catalyst, the improvement wherein said catalyst comprises (A) a substantially catalytically inert carrier, and
(B) supported thereon, from 0.005 to 1 g in total, per gram of the carrier, of catalyst components comprising (i) a copper component, (ii) a zinc component, and optionally (iii) at least one metal component selected from aluminum, chromium, vanadium, magnesium and manganese.

18 Claims, No Drawings

PROCESS FOR PREPARATION OF METHANOL

This application is a continuation of now abandoned application Ser. No. 344,932, filed 02/02/82.

This invention relates to a process for the preparation of methanol. More specifically, it relates to an improvement in and relating to a process for the preparation of methanol by reacting a gaseous mixture comprising hydrogen and either one or both of carbon monoxide and carbon dioxide in the gaseous phase in the presence of a catalyst based on copper and zinc.

It has been known to use a catalyst composed of copper and zinc as main ingredients and a third co-catalyst component in the synthesis of methanol from a gaseous mixture of hydrogen and one or both of carbon monoxide and carbon dioxide. This type of catalyst has previously been produced by a method which comprises (a) kneading catalytic compounds such as powdery copper oxide or copper chromite and zinc oxide with an aqueous solution of chromic acid or (b) co-precipitating catalytic compounds from an aqueous solutions of water-soluble copper and zinc compounds by using a suitable precipitant; and thereafter molding the resulting mixture of the catalytic compounds by a tableting machine either as such or after calcining it, optionally after adding molding agents. No method has previously been practiced which involves supporting catalytically active materials on a carrier material. Accordingly, the catalyst tablets obtained by this conventional method are composed entirely of the catalytically active materials except the molding agents.

In recent years, with an increase in the scale of the methanol industry, the amount of the catalyst to be filled in a reactor has become enormous. Accordingly, the cost of charging and exchanging the catalyst has risen strikingly, and the amount of losses will be huge in the event the accident of catalyst deactivation should happen owing to a trouble in the equipment. Thus, the increased cost and risk incident to the use of catalyst in a large-sized apparatus give rise to a new problem in the methanol synthesis industry, and it has been desired to develop means of solving this problem.

The present inventor worked extensively on the mechanism of exhibition of the effect of a catalyst. As a result, they found that in a conventional tableted catalyst, only the very limited surface layer portion of the catalyst tablet acts as a catalyst, and the inside of the tablet does not act as a catalyst but serves substantially as a carrier. Based on this finding, he assumed that the inside of the catalyst tablet would be able to be replaced by an ordinary inert carrier material. On further investigation, this assumption has been determined experimentally to be correct.

According to this invention, there is provided, in a process for preparing methanol which comprises reacting a gaseous mixture containing hydrogen and either one or both of carbon monoxide and carbon dioxide in the gaseous phase in the presence of a catalyst, the improvement wherein said catalyst comprises (A) a substantially catalytically inert carrier, and (B) supported thereon, from 0.005 to 1 g in total, per gram of the carrier, of catalyst components comprising (i) a copper component, (ii) a zinc component, and optionally (iii) at least one metal component selected from aluminum, chromium, vanadium, magnesium and manganese.

The supported catalyst used in the process of this invention, has an equivalent or higher catalytic activity to or than conventional non-supported catalysts. In addition, although conventional supported catalysts have generally been considered to have poor durability of catalytic activity, the supported catalyst used in this invention unexpectedly has the advantage that its catalytic activity lasts for an extended period of time.

There is no particular restriction on the kind and material of the carrier of the supported catalyst used in this invention so long as it is substantially inert to the methanol synthesizing reaction in accordance with this invention. Thus, any carrier materials can be used which have previously been used to support catalytically active substances. Suitable carrier materials are porous and have a high specific surface area of usually about 0.1 to about 600 $m^2/g$, preferably about 0.1 to about 300 $m^2/g$. Specific examples of such carrier materials include alpha-alumina, silica, silica-alumina, natural zeolite, synthetic zeolites, ceramics, silicon carbide, procelains, unglazed ceramics, diatomaceous earth, pumice, titanium oxide, zirconia, alundum and steatite. Of these, alpha-alumina, silica-alumina, silicon carbide and pumice are especially suitable. The shape and size (particle size) of the carrier material need to be varied depending upon some factors such as the size and internal structure of a reactor used, the type of a catalyst layer (whether it is a fixed or fluidized bed), etc. In the case of a fixed bed which is now commonplace today in the synthesis of methanol, the carrier is advantageously in the form of a sphere having a diameter of 3 to 10 mm, a cylinder having a diameter of 3 to 10 mm and a length of 2 to 10 mm, or a Raschig ring having a particle size of about 3 to about 15 mm.

Deposition of the catalystically active components, i.e. (i) the copper component, (ii) the zinc component and optionally (iii) the other metal component can be carried out by various methods known per se. For example, it can be carried out by an impregnation method, a coating method, or a combination of these.

For example, when the supported catalyst of this invention is prepared by the impregnation method, the catalytically active components can be deposited on the carrier material by dipping the carrier material in a homogeneous aqueous solution of a copper-containing water-soluble compound and a zinc-containing water-soluble compound and as required, a water-soluble compound of the other metal at room temperature or an elevated temperature of up to about 100° C. and an atmospheric pressure or a reduced pressure of not less than about 20 mgHg. Examples of the copper-containing water-soluble compound which can be used in the impregnation method include copper nitrate, copper salts of organic acids such as copper acetate, and an ammine complex of copper. On the other hand, examples of the zinc-containing water-soluble compounds include zinc nitrate, zinc salts of organic acids such as zinc acetate, and an ammine complex of zine. Examples of the water-soluble compound of the other metal include nitrates, organic acid salts, and an ammine complex of the other metals.

Desirably, the above water-soluble compounds are easily oxidized to the oxides of the respective metals or reduced into elemental metals when subjected to the following calcination or reduction conditions. It is further desirable that these water-soluble compounds should not contain a catalyst poison such as halogen or sulfur.

The concentration of each of these water-soluble compounds in the aqueous solution can be varied widely depending upon the amount of each catalytically active component to be supported on the carrier material. Generally, the concentration is in the range of 0.1 mole/liter to 3 moles/liter, and the relative concentrations of the individual compounds are adjusted to correspond nearly to the metal atomic ratios to be described hereinbelow.

The dipped carrier material is separated from the aqueous solution, and dried in the air or in an atmosphere of an inert gas such as nitrogen at a temperature of about 70° to about 130° C. Then, the impregnated product, either as such or after calcination, is subjected to a reducing treatment in an atmosphere of a reducing gas such as hydrogen gas, carbon monoxide gas, a gaseous mixture of hydrogen and either one or both of carbon monoxide and carbon dioxide, or any of these gases diluted with an inert gas such as nitrogen, thereby giving the desired catalyst. The calcination may generally be carried out in the air or in an atmosphere of nitrogen, etc. at a temperature of about 300° to about 550° C., preferably about 350° to about 400° C., for a period of about 0.5 to about 5 hours. The calcination results in the conversion of the copper component, zinc component and other metal component to oxides of the respective metals.

The reduction, on the other hand, may be carried out at a temperature of about 120° to about 300° C., preferably about 140° to about 250° C. and a pressure of about 1 to about 30 kg/cm$^2$, preferably about 1 to about 3 kg/cm$^2$, until the supported metallic components are rendered catalytically active (namely, until most of them are reduced to the elemental metals). The reducing treatment may be carried out independently of the methanol synthesizing reaction, although it is industrially preferred to perform it as a pre-stage of the methanol synthesizing reaction after the supported catalyst has been charged into a reactor for methanol synthesis.

On the other hand, the coating method for preparation of the supported catalyst in accordance with this invention may be carried out, for example, by contacting an aqueous slurry (which may contain a surface-active agent for increasing the stability of the slurry) containing water-insoluble or sparingly water-soluble copper and zinc compounds and optionally other metal compounds with the carrier material at room temperature or an elevated temperature of up to about 100° C.; or pre-heating the carrier material to a temperature of about 300° to about 550° C. and spraying the aforesaid aqueous slurry to the pre-heated carrier material. In the former method, the carrier material is dried in the same way as in the impregnation method after contacting, optionally calcined, and then subjected to the reducing treatment to give the desired active catalyst. This catalyst can immediately be used in the synthesis of methanol. In the case of the latter spraying method, the coated carrier material is calcined depending upon the pre-heating temperature used to pre-heat the carrier material (when the calcination temperature agrees with the pre-heating temperature, the calcination may be omitted), and then subjected to the aforesaid reducing treatment to give the desired active catalyst which can immediately be used in the synthesis of methanol.

Examples of the water-insoluble or sparingly water-soluble compounds of copper, zinc and other metals which can be used in the above coating method are basic carbonates and hydroxides of these metals.

The concentration of each of these metal compounds in the above aqueous slurry or the aqueous paste is 5 to 25% by weight.

For purposes of this invention, the term "supported catalyst", as used herein, denotes not only a catalyst in which the individual metal components supported on the carrier are substantially catalytically active, but also a catalyst precursor in which the individual metal components on the carrier can be easily rendered catalytically active by the aforesaid combination of calcination and reduction or only by the reducing treatment.

The supported catalyst used in this invention may contain the copper and zinc components in such proportions that the Cu/Zn atomic ratio is generally from 98/2 to 20/80, preferably 98/2 to 30/70. The amount of the other metal component as a third optional component to be deposited differs depending upon the type of the elemental metal. For example, it is expressed by an Al/(Cu+Zn) atomic ratio of generally from 300/100 to 1/100, preferably 50/100 to 5/100, for aluminum; a Cr/(Cu+Zn) atomic ratio of generally from 1/100 to 100/100, preferably from 5/100 to 50/100, for chromium; a V/(Cu+Zn) atomic ratio of generally from 0.5/100 to 30/100, preferably from 1/100 to 20/100, for vanadium; a Mg/(Cu+Zn) atomic ratio of generally from 0.1/100 to 15/100, preferably from 1/100 to 5/100, for magnesium; and a Mn/(Cu+Zn) atomic ratio of generally from 0.1/100 to 30/100, preferably from 1/100 to 15/100, for manganese.

After the aforesaid calcination treatment, total amount of these metallic catalyst components can be adjusted to 0.005 to 1 g, preferably 0.01 to 0.5 g, per gram of the carrier. Desirably, these catalyst components are present so as to substantially completely and uniformly cover the surface of the carrier. In order to obtain a catalyst having excellent activity, the thickness of the catalyst component layer is desirably 0.01 to 1.0 mm preferably from 0.1 to 0.3 mm.

The final supported catalyst reduced to an active state is used in accordance with the process of this invention as a catalyst for synthesizing methanol from a gaseous mixture containing hydrogen and either one or both of carbon monoxide and carbon dioxide.

The methanol synthesizing reaction using the supported catalyst in accordance with this invention may be carried out by any method known per se, for example the method described in U.S. Pat. No. 3,971,735. For example, it is carried out by feeding the aforesaid gaseous mixture over the catalyst bed at a temperature of 150° to 300° C., preferably 200° to 280° C. and a pressure of 20 to 300 atmospheres, preferably 30 to 150 atmospheres, at a space velocity of 2,000 to 80,000 hr$^{-1}$.

The starting gaseous mixture for the production of methanol in the presence of the supported catalyst in accordance with this invention may be a gaseous mixture of the composition previously used in the art, and there is no particular restriction on the composition of the starting gaseous mixture in this invention.

The supported catalyst used in the process of this invention has the unexpected advantage that in spite of the fact that its the amount of the catalyst components is much smaller than that of a conventional tableted catalyst (e.g., from 1:several to 1:several tens by ratio), the catalytic activity of the supported catalyst of this invention per unit volume is equal to, or larger than, the tableted catalyst containing the same types of the catalytically active substances as the supported catalyst.

The following examples illustrate the present invention more specifically.

[A] Comparison with a known Cu—Zn catalyst (Japanese Patent Publication No. 7574/71)

REFERENTIAL EXAMPLE 1

Water (140 ml) was added to a mixture of 43.2 g of basic copper carbonate (analytical grade) and 41.0 g of basic zinc carbonate (analytical grade) (Cu/Zn atomic ratio=1), and the mixture was kneaded for three hours to form a paste. The paste was divided into two equal portions. One of the portions (the other used in Example 1) was dried overnight at 80° C., and calcined at 300° C. for 3 hours in a flow of nitrogen. Then, using graphite as a lubricant, the calcined product was tableted into cylindrical tablets 6 mm in diameter and 6 mm in height. The individual tablets were each divided into 8 portions by cutting each of them longitudinally and transversely, and treated with a gaseous mixture of carbon monoxide and hydrogen at 200° C. for 3 hours to perform reduction and activation. The resulting catalyst tablets are designated as a catalyst A'.

EXAMPLE 1

To the other portion of division obtained in Referential Example 1 were added 25 g of alumina sol containing 10% by weight of alumina and 120 ml of water. These materials were vigorously stirred by a mixer to form a stable slurry. The slurry was transferred into a sprayer. A part of the slurry was intermittently sprayed onto 50 ml of a sintered spherical silicon carbide carrier, 3 mm in diameter, maintained at 250° C. in a rotary dryer to deposit the catalyst components on it. The carrier having the catalyst components deposited thereon was then calcined at 380° C. for 1 hour, and thereafter treated with a gaseous mixture of carbon monoxide and hydrogen at 150° C. for 2 hours in the same way as in Referential Example 1 for reduction and activation. The resulting catalyst is designated as a catalyst A.

[B] Comparison with a known Cu—Zn—Al catalyst (British Pat. No. 1,286,970)

REFERENTIAL EXAMPLE 2

Zinc nitrate crystals (1820 g) and 760 g of copper nitrate crystals were dissolved in 3200 ml of water, and the solution was mixed at 60° C. with an aqueous solution of sodium carbonate (1 mole/liter) in an amount which would adjust the pH of the resulting mixture to 6.8 to precipitate a mixture of basic zinc carbonate and basic copper carbonate. The precipitate was collected by filtration, washed, and then divided into two equal portions. One of the portions (the other used in Example 2) was dried and then calcined at 380° C. for 2 hours. A blender was charged with 240 g of the calcined product, and 160 g of alumina trihydrate and 1920 ml of water were added. The blender was then operated to mix these materials well. The mixture was then dried, and tableted into tablets, 6 mm in diameter and 6 mm in height, which were then calcined at 380° C. for 2 hours. After the calcination, the individual tablets were divided into eight portions in the same way as in Referential Example 1, and treated with a gaseous mixture of carbon monoxide and hydrogen at below 260° C. for reduction. The resulting catalyst is designated as a catalyst B'.

EXAMPLE 2

The other portion of division obtained in Referential Example 2 was taken into a mixer, and 250 g of alumina trihydrate and 1000 ml of water were added. Furthermore, to improve the stability of the slurry, 100 g of the same alumina sol as used in Example 1 was added. They were mixed under vigorous stirring. A part of the resulting slurry was transferred into a sprayer. A part of the slurry in the sprayer was intermittently sprayed onto 50 ml of a sintered spherical alpha-alumina carrier (3 mm in diameter) maintained at 350° C. in a rotary dryer to deposit the catalyst components on it. After the spraying, the product was left to stand at 350° C. in the rotary dryer for 30 minutes. Then, it was taken out from the dryer and without calcination, treated with a gaseous mixture of carbon monoxide and hydrogen in the same way as in Example 1 for reduction and activation. The resulting catalyst is designated as a catalyst B.

[C] Comparison with a known Cu—Zn—V catalyst (U.S. Pat. No. 3,818,067)

REFERENTIAL EXAMPLE 3

A solution (A) of 725 g of copper nitrate crystals and 446 g of zinc nitrate crystals in 9 liters of water and a solution (B) of 70 g of $NaVO_3.H_2O$ and 450 g of sodium carbonate in 9 liters of water were prepared, and then heated individually at 80° to 90° C. The solution (A) was added to the solution (B) with vigorous stirring to form a precipitate. The precipitate was collected by filtration, and washed with 50 liters of warm water. The cake was divided into two equal portions. One of the portions (the other used in Example 3) was dried at 110° C., and calcined at 300° C. for 5 hours. Then, 2% of graphite was added, and the mixture was tableted into tablets 6 mm in diameter and 6 mm in height. The tablets in a required amount were divided into 8 portions in the same way as in Referential Example 1, and treated with a gaseous mixture of carbon monoxide and hydrogen for 5 hours for reduction. The resulting catalyst is designated as a catalyst C'.

EXAMPLE 3

200 g of the cake was taken from the other portion of division obtained in Referential Example 3, and put in a mixer. Then, 150 ml of water and 20 g of the same alumina sol as used in Example 1 for improving stability of the slurry were added. They were mixed with vigorous stirring to form a slurry. The slurry was transferred into a sprayer, and a part of the slurry was intermittently sprayed onto 50 ml of a spherical ceramic carrier 3 mm in diameter maintained at 150° C. in a rotary dryer to deposit the catalyst components on it. After the deposition, the product was calcined at 350° C. for 1 hour, and then subjected to the same reducing treatment as in Example 1 to form a catalyst which is designated as a catalyst C.

[D] Comparison with a known Cu—Zn—Cr catalyst (U.S. Pat. No. 3,256,208)

REFERENTIAL EXAMPLE 4

Chromic anhydride (75 g) was dissolved in 75 ml of water, and 78 g of a product obtained by thermally decomposing basic copper ammonium chromate at 300° C. for 1 hour, and then 122 g of zinc oxide rendered paste-like with water was added. The mixture was kneaded for 1 hour to form a uniform paste. The paste was shaped into a plate form having a thickness of 5 to 6 mm in a Petri dish, dried at 60° C., and then pulverized to a particle diameter of about 6 mm. The particles were then treated with a gaseous mixture of carbon monoxide and hydrogen at 230° C. for 5 hours for reduction and activation. The resulting catalyst is designated as a catalyst D'.

EXAMPLE 4

Chromic anhydride (75 g) was dissolved in 75 ml of water, and 78 g of the same thermal decomposition product of basic copper ammonium chromate as used in Referential Example 4 was added. The mixture was kneaded for 1 hour, and then 150 ml of a slurry prepared from 122 g of zinc oxide and a 1% aqueous solution of soluble starch was added. The mixture was kneaded for 1 hour. In order to make the state of the paste suitable for coating on a carrier, a moderate amount of the above aqueous solution of soluble starch was added, and the mixture was kneaded for 15 minutes. The resulting paste was deposited on 50 ml each of a cylindrical silica alumina carrier 2 mm in diameter and 3 mm in height, a porcelain carrier 3 mm in diameter, and an irregularly-shaped pumice carrier having a particle diameter of 3 mm, respectively, at room temperature. The deposition was effected by mixing 350 ml of the original carrier and a suitable amount of the paste at room temperature to coat the carrier with the paste, and then drying the coated carrier at 60° C. Each of the supported catalysts obtained was treated with a gaseous mixture of carbon monoxide and hydrogen at 180° to 240° C. for 2 hours to provide a catalyst D-1 comprising the silica alumina carrier, a catalyst D-2 containing the porcelain carrier, and a catalyst D-3 containing the pumice carrier, respectively.

[E] Cu—Zn—Mn catalyst

REFERENTIAL EXAMPLE 5

A stainless steel (SUS 304) container equipped with a stirrer was charged with 6000 ml of an aqueous solution containing 318.0 g of sodium carbonate of analytical grade (to be referred to as an aqueous precipitant solution), and heated to 70° C.

Separately, a stainless steel (SUS 304) container equipped with a ball valve at its bottom was charged with 5000 ml of an aqueous solution containing 402.5 g of copper nitrate (analytical grade), 212.5 g of zinc nitrate (analytical grade) and 34.0 g of manganese nitrate (analytical grade) (to be referred to as an aqueous component solution). The container was placed at a position which would permit flowing of the aqueous component solution into the aqueous precipitant solution upon opening of the ball valve, and was heated to 70° C.

While the aqueous precipitant solution was vigorously stirred, the ball valve was completely opened to let all the aqueous component solution fall into the precipitant solution and be mixed to form a precipitate. Then, with stirring, the temperature of the solution was maintained at 70° C. for 1.5 hours. The mixture was further stirred for 1 hour while allowing it to cool. The precipitate was collected by filtration and washed.

The resulting cake was divided into two equal portions. One of the portions (the other used in Example 5) was dried overnight at 80° C., and calcined at 380° C. for 1.5 hours in a stream of air. Then, 2% by weight of graphite was added, and the mixture was tableted into cyclindrical tablets 6 mm in diameter and 6 mm in height. The tablets were each divided into 8 portions in the same way as in Referential Example 1, and treated with a gaseous mixture of carbon monoxide and hydrogen for reduction. The resulting catalyst is designated as a catalyst E'.

EXAMPLE 5

200 g of the cake was taken from the other portion of division obtained in Referential Example 5, and put in a mixer. Water (200 ml) and 50 ml of a 1% aqueous solution of soluble starch for improving the stability of the resulting slurry were added. They were mixed with vigorous stirring to form a slurry. The slurry was transferred into a sprayer, and a part of it was intermittently sprayed onto 50 ml of a 4-8 mesh steatite carrier maintained at 220° C. in a rotary dryer to deposit the catalyst components. After the deposition, the product was calcined at 380° C. for 1.5 hours in a stream of air, and then subjected to the same reducing treatment as in Example 1. The resulting catalyst is designated as a catalyst E.

[F] Cu—Zn—Mg catalyst

REFERENTIAL EXAMPLE 6

The same stainless steel (SUS 304) container equipped with a stirrer as used in Referential Example 5 was charged with 6000 ml of an aqueous solution containing 310.0 g of sodium carbonate (analytical grade) (to be referred to as an aqueous precipitant solution), and heated to 70° C.

Separately, the same stainless steel (SUS 304) container equipped with a ball valve as used in Referential Example 5 was charged with 5000 ml of an aqueous solution (to be referred to as an aqueous component solution) containing 402.5 g of copper nitrate (analytical grade), 212.5 g of zinc nitrate (analytical grade) and 30.5 g of magnesium nitrate (analytical grade), and heated to 70° C.

While the aqueous precipitant solution was vigorously stirred, the ball valve of the container located above it was opened to let all the aqueous component solution fall into the precipitant solution and be mixed to form a precipitate. With stirring, the temperature of the solution was maintained at 70° C. for 2.5 hours. The precipitate was collected by filtration, and washed with water, and the adhering water was freed. The cake was then divided into two equal portions.

One of the portions (the other used in Example 6) was dried overnight at 80° C., and calcined at 380° C. for 1.5 hours in a stream of air. Then, 2% by weight of graphite was added, and the mixture was compression-molded into cylindrical tablets 6 mm in diameter and 6 mm in height. In the same way as in Referential Example 1, the tablets were divided into eight portions, and treated with a gaseous mixture of carbon monoxide and hydrogen for reduction. The resulting catalyst is designated as a catalyst F'.

EXAMPLE 6

200 g of the cake was taken from the other portion of division obtained in Referential Example 6, and 50 ml of a 1% aqueous solution of soluble starch and 250 ml of water were added. They were mixed with vigorous stirring to form a homogeneous slurry. The slurry was transferred into a sprayer, and intermittently sprayed onto 50 ml of a spherical unglazed ceramic carrier 3 mm in diameter maintained at 180° C. in a rotary dryer to deposit the catalyst components. After the deposition, the product was calcined at 380° C. for 1.5 hours in a stream of air, and then subjected to the same reducing treatment as in Example 1 to provide a catalyst which is designated as a catalyst F.

Test for Synthesis of Methanol

Using 30 ml of each of the catalysts obtained as above a test was conducted for catalyst activity in the synthesis of methanol. Specifically, a starting gaseous mixture consisting of 64.7% of $H_2$, 6.5% of CO, 4.3% of $CO_2$, 22.0% of $CH_4$ and 2.5% of $N_2$ was reacted in the presence of the catalyst at 270° C. and an SV of 10000 $hr^{-1}$. The performance of the catalyst, in terms of the concentration of methanol in the off-gas, is shown in Table 1.

Table 1 also shows the weight of the catalytically active substances in 30 ml of each of the catalysts used in the activity test.

It is seen from the results shown in Table 1 that the supported catalysts of this invention have equivalent or higher activity to or than conventional unsupported catalysts in spite of the fact that the amount of the catalytically active substances is about one-tenth of that of the catalytically active substances in the conventional unsupported catalysts.

TABLE 1

| Runs (*) | Catalyst | Carrier | Metal components of catalytically active substances | Amount of the catalytically active substances per 30 ml of the catalyst (g) | Methanol concentration of the outlet gas at 270° C. (mole %) |
|---|---|---|---|---|---|
| REx. 1 | A' | None | Cu—Zn | 35 | 4.8 |
| Ex. 1 | A | Spherical silicon carbide | Cu—Zn | 2.4 | 5.2 |
| REx. 2 | B' | None | Cu—Zn—Al | 32 | 3.6 |
| Ex. 2 | B | Spherical alpha-alumina | Cu—Zn—Al | 3.6 | 3.8 |
| REx. 3 | C' | None | Cu—Zn—V | 34 | 5.0 |
| Ex. 3 | C | Spherical ceramics | Cu—Zn—V | 4.1 | 5.3 |
| REx. 4 | D' | None | Cu—Zn—Cr | 30 | 2.7 |
| Ex. 4 | D-1 | Cylindrical silica-alumina | Cu—Zn—Cr | 4.3 | 2.8 |
| Ex. 4 | D-2 | Spherical porcelain | Cu—Zn—Cr | 2.7 | 2.7 |
| Ex. 4 | D-3 | Irregularly-shaped pumice | Cu—Zn—Cr | 3.8 | 3.0 |
| REx. 5 | E' | None | Cu—Zn—Mn | 35 | 4.8 |
| Ex. 5 | E | Steatite | Cu—Zn—Mn | 5.0 | 5.3 |
| REx. 6 | F' | None | Cu—Zn—Mg | 33 | 5.1 |
| Ex. 6 | F | Spherical unglazed ceramics | Cu—Zn—Mg | 4.3 | 5.7 |

(*) REx. = Referential Example; Ex. = Example

What is claimed is:

1. In a process for preparing methanol which comprises reacting a gaseous mixture containing hydrogen and either one or both of carbon monoxide and carbon dioxide in the gaseous phase in the presence of a catalyst, the improvement wherein said catalyst comprises
   (A) a substantially catalytically inert carrier in the form of spheres of 3 to 10 mm diameter, cylinders of 3 to 10 mm diameter and length of 2 to 10 mm or Raschig rings having a size of about 3 to about 15 mm and,
   (B) supported thereon, in a thickness of 0.01 to 1.0 mm on the surface of the carrier, from 0.005 to 1 g in total, per gram of the carrier, of catalyst components comprising (i) a copper component, (ii) a zinc component, and optionally (iii) at least one metal component selected from aluminum, chromium, vanadium, magnesium and manganese.

2. The process of claim 1 wherein the total amount of the catalyst components in the catalyst is from 0.01 to 0.5 g per gram of the carrier.

3. The process of claim 1 wherein the copper component and the zinc component are supported on the carrier in a Cu/Zn atomic ratio in the range of from 98/2 to 20/80.

4. The process of claim 1 wherein said other metal component is an aluminum component.

5. The process of claim 4 wherein the aluminum component is supported on the carrier in such a proportion that the Al/(Cu+Zn) atomic ratio is in the range of from 300/100 to 1/100.

6. The process of claim 1 wherein said other metal component is a chromium component.

7. The process of claim 6 wherein the chromium component is supported on the carrier in such a proportion that the Cr/(Cu+Zn) atomic ratio is in the range of from 1/100 to 100/100.

8. The process of claim 1 wherein said other metal component is a vanadium component.

9. The process of claim 8 wherein the vanadium component is supported on the carrier in such a proportion that the V/(Cu+Zn) atomic ratio is in the range of from 0.5/100 to 30/100.

10. The process of claim 1 wherein said other metal component is a magnesium component.

11. The process of claim 10 wherein the magnesium component is supported on the carrier in such a proportion that the Mg/(Cu+Zn) atomic ratio is in the range of from 0.1/100 to 15/100.

12. The process of claim 1 wherein said other metal component is a manganese component.

13. The process of claim 12 wherein the manganese component is supported on the carrier in such a proportion that the Mn/(Cu+Zn) atomic ratio is in the range of from 0.1/100 to 30/100.

14. The process of claim 1 wherein said copper component is copper, an oxide of copper, or a mixture of these.

15. The process of claim 1 wherein said Zinc component is zinc, an oxide of zinc, or a mixture of these.

16. The process of claim 1 wherein said metal component is the metal, an oxide of the metal, or a mixture of these.

17. The process of claim 1 wherein said carrier is selected from the group consisting of alpha-alumina, silica, silica-alumina, natural zeolite, synthetic zeolites, ceramics, silicon carbide, porcelains, unglazed ceramics, diatomaceous earth, pumice, titanium oxide, zirconia, alundum and steatite.

18. The process of claim 1 wherein the reaction is carried out at a temperature of 150° to 300° C. and a pressure of 20 to 300 $kg/cm^2$.

* * * * *